(12) United States Patent
Shukla et al.

(10) Patent No.: US 6,451,356 B1
(45) Date of Patent: Sep. 17, 2002

(54) **ANTIBACTERIAL COMPOSITION COMPRISING OENOSTACIN FROM *OENOTHERA BIENNIS***

(75) Inventors: Yogendra Nath Shukla; Tiruppadiripuliyur Ranganathan Santha Kumar; Anil Srivastava; Suman Preet Singh Khanuja; Vivek Kumar Gupta; Sushil Kumar, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/081,195

(22) Filed: Feb. 22, 2002

Related U.S. Application Data

(62) Division of application No. 09/666,770, filed on Sep. 21, 2000, now Pat. No. 6,365,177.

(51) Int. Cl.[7] ............................................... A61K 35/78
(52) U.S. Cl. ........................ 424/725; 424/405; 514/163
(58) Field of Search ................................ 424/725, 405; 514/163

(56) References Cited

PUBLICATIONS

*J. Med. Arom. Plant Sci.,* 20:432, 1998.
*Z Phytother,* 4531, (Mar. 1983), Nr. 2.
*J. Am. Oil Chem. Soc.,* 61:540, 1984.
*Riv Ital Sastanze Grasse,* 53:25, 1976.
*Phytochemistry,* 6:317, 1967.
*Chem Pharm Bull,* 39:1157, 1991.
*Indian Journal of Chemistry,* vol. 38B, pp. 705–708, 1999.
Bauer, et al., *American Journal of Clinical Pathology,* 45:493–496, 1966.
Skula et al. Indian Drugs (Jan. 2000) vol. 37, No. 1, pp. 60–61.

*Primary Examiner*—Francisco Prats
*Assistant Examiner*—Susan D. Coe
(74) *Attorney, Agent, or Firm*—McDonnell Boehnen Hulbert & Berghoff

(57) ABSTRACT

The present invention provides a pharmaceutical composition for treating bacterial infections in patients comprising an effective amount of 3.5-dihydroxy-4-pent-4'-enoyl-1'-oxymethylbenzoic acid (Oenostacin) isolated from *Oenothera biennis*.

5 Claims, No Drawings

US 6,451,356 B1

ANTIBACTERIAL COMPOSITION COMPRISING OENOSTACIN FROM *OENOTHERA BIENNIS*

This is a divisional of application Ser. No. 09/666,770, filed on Sep. 21, 2000 now U.S. Pat. No. 6,365,197, issued Sep. 21, 2000.

BACKGROUND OF THE INVENTION

1. Field of Invention

This invention relates to the use of a compound 3,5-dihydroxy-4-pent-4'-enoyl-1'-oxymethylbenzoic acid (Oenostacin) isolated from the roots of the plant *Oenothera biennis* as an effective antibacterial agent active against bacteria such as staphylococci, streptococci and the like. The invention also provides pharmaceutical compositions comprising 3,5-dihydroxy-4-pent-4'-enoyl-1'-oxymethylbenzoic acid (Oenostacin) useful for treatment of skin infections such as endocarditis in humans caused by *Staphylococcus epidermidis*.

2. Summary of the Related Art

The antimicrobial era has reached a point where the emergence of resistant microbes is accelerating while the pace of discovery of new drugs seems decelerating (*Science* 157:1064–1073). Until recently, drugs or combination of drugs have not been able to overcome the problem of resistance. Few novel chemical entities have been brought to the market during the past decade to address this problem, as most of the new drugs are derivatives of older compounds. Many of these have increased activity or a broader spectrum of activity or improved pharmacological properties but can only temporarily overcome the problem of resistance. Thus, the isolation of natural products from sources such as various species of plants has become a basis for identifying new class of antimicrobial compounds. These compounds are being investigated for treatment of infections caused during seemingly uncomplicated hospital treatment procedures such as catheterization, insertion of intrauterine contraceptive devices and intravenous injections, for example.

Inflammation of the endocardium, i.e., the tissue lining of the cavities of the heart, is called endocarditis. Infective (infectious) endocarditis may be due to infection by a range of microorganisms such as Haemophilus sp., *Staphylococcus aureus, Sepidermidis* (especially in patients with prosthetic valves), *Streptococcus faecalis, Neisseria gonorrhae*, Candida, etc. Infective endocarditis may be acute (e.g, when due to streptococci or gonococci) or sub-acute when due to viridans streptococci or fungi. Infection occurs through the circulatory system and organisms may gain access to the blood stream during dental treatment, catheterization, insertion of intrauterine contraceptive devices or intravenous injections, for example. The symptoms associated with such infections include fever, malaise, heart murmurs, weight loss, clubbing of fingertips and embolism. Late symptoms of sub-acute bacterial endocarditis include vasculitis, petechial rash and Osler's nodes. In addition, damage to heart valves may lead to heart failure. Endocarditis may also occur as a complication of other infectious diseases.

*Oenothera biennis* (Onagraceae) is a genus of herbs and undershrubs distributed mainly in temperate America together with some species occurring in the tropics. Some of the species including *O. biennis* have been introduced into Indian Gardens (*J.Med.Arom Plant Sci.*, 20:1998, 432). The oil from seeds of *O. biennis* (Evening Primrose) is known to be a rich dietary source of γ-linolenic acid required for the formation of prostaglandins and related hormones (*Z Phytother*, 4:1983, 531). The seeds are reported to contain fatty acids (*J. Am Oil Chem Soc*, 61:1984, 540) and sterols (*Riv Ital Sastanze Grasse*, 53, 1976,25) while the leaves contain flavonoids (*Phytochemistry*, 6:1967, 317) and Oenothein A (*Chem Pharm Bull*, 39:1991, 1157). However, no compounds have been reported from the roots of *O.biennis*. Recently, certain specific activity is observed in the root extracts and this prompted a systematic activity-directed fractionation to isolate pure compounds. This systemic activity-directed fractionation of root extracts resulted in the identification of ten compounds, four of which are novel and reported in the *Indian Journal of Chemistry*, Vol. 38B, 1999, pages 705–708.

SUMMARY OF THE INVENTION

It is therefore an object of the invention to provide a compound that has potent activity as an antibacterial agent.

It is further an object of the invention to provide a pharmaceutical composition comprising a potent antibacterial agent.

Yet another object of the invention is to provide a method for the treatment of bacterial infections, especially diseases caused by bacteria.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.1

Accordingly, the present invention provides the compound 3,5-dihydroxy-4-pent-4'-enoyl-1'-oxymethylbenzoic acid (Oenostacin) as an antibacterial agent (*Indian Journal of Chemistry*, Vol. 38B, 1999, pages 705–708, incorporated herein by reference). This chemical compound has the molecular formula $C_{13}H_{14}O_6$ and the structural formula:

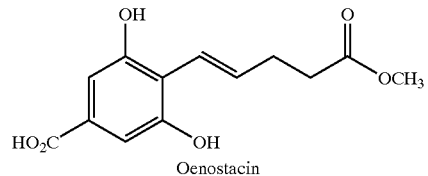

Oenostacin

In a preferred embodiment, Oenostacin is active against streptococci and staphylococci, especially *Staphylococcus epidermidis*, which causes skin infections/endocarditis in humans. Hence, the present invention provides an antibiotic isolated from the roots of the plant *O. biennis* for use against *S. epidermidis* infection.

The invention further provides a pharmaceutical composition having antibacterial activity, comprising Oenostacin in combination, admixture, or associated with a pharmaceutically acceptable carrier, diluent or excipient thereof.

The invention also provides a method of treating a bacterial infection, and preferably a bacterial skin infection, comprising administering to a patient with such an infection an effective amount of Oenostacin.

DETAILED DESCRIPTION OF THE INVENTION

Accordingly, the invention provides a novel antibacterial composition comprising an effective amount of Oenostacin (3,5-dihydroxy-4-pent-4'-enoyl-1'-oxymethylbenzoic acid) obtained from the roots of *Oenothera biennis* in combination, admixture, or associated with a pharmaceutically acceptable carrier, diluent or excipient thereof.

In an embodiment of the invention, the 3,5-dihydroxy-4-pent-4'-enoyl-1'-oxymethylbenzoic acid is an extract obtained from the plant *Oenothera biennis* (*Indian Journal of Chemistry*, Vol. 38B, 1999, pages 705–708).

The concentration of Oenostacin in the composition is in the range of 1–200 μg/ml, or in the range of 10–90% by weight.

The antibacterial composition is effective against bacteria selected from streptococci, staphylococci and *Pseudomonas aeruginosa*, and preferably streptococci and staphylococci. The antibacterial composition may further be used for the treatment of endocarditis in humans. Acute endocarditis is an inflammatory disease of the endocardium i.e., the internal lining of the human heart and may be caused by the staphylococci and gonococoi bacteria, for example. Among staphylococci, *S.epidermidis* is one of the major etiological agents of this disease. The infections occur mainly in-patients with prosthetic valves.

Thus, the antibacterial composition may be used for the treatment of infections caused by *S. epidennidis*.

Using a screening program aimed at detecting biomolecules from plant sources, which can specifically act against *S. epidermidis*, the present inventors have now discovered that the ethanolic extract derived from the roots of a plant called *O. biennis* contains the compound 3,5-dihydroxy-4-pent-4'-enoyl-1'-oxymethylbenzoic acid, which possesses antibacterial activity. *Oenothera biennis* is a genus of herbs and under-shrubs; its species mainly distributed in temperate America together with some species occurring in the tropics. Some of the species such as *O. biennis* have been introduced into the Indian gardens. The seeds of the plant are rich source of fatty acids and sterols required for the formation of prostaglandins and other hormones. A systematic activity-directed fractionation of root extracts resulted in the identification of ten compounds, four of which are new (*Indian Journal of Chemistry*, Vol. 38B, 1999, pages 705–708).

In a preferred extraction process, the air-dried powdered roots of *O.biennis* are extracted with MeOH. Water is then added and the extract is then fractionated successively into n-hexane, ethyl acetate (EtOAc) and n-BuOH. Silica gel column chromatography of the n-hexane and EtOAc fraction yields many known compounds, such as gallic acid (CIM 790), and a new compound (CIM 791) further identified by NMR. This compound is found to possess strong activity against *Staphylococcus epidennidis* and is named Oenostacin. Table 1 describes the general procedure followed for the bioactivity-guided fractionation of the isolate active compounds of *O.biennis*. Here, bioactivity-guided fractionation is employed to isolate the active principle involved in the inhibition of *S.epidermidis* growth.

TABLE 1

ACTIVITY GUIDED FRACTIONATION OF *Oenothera biennis*

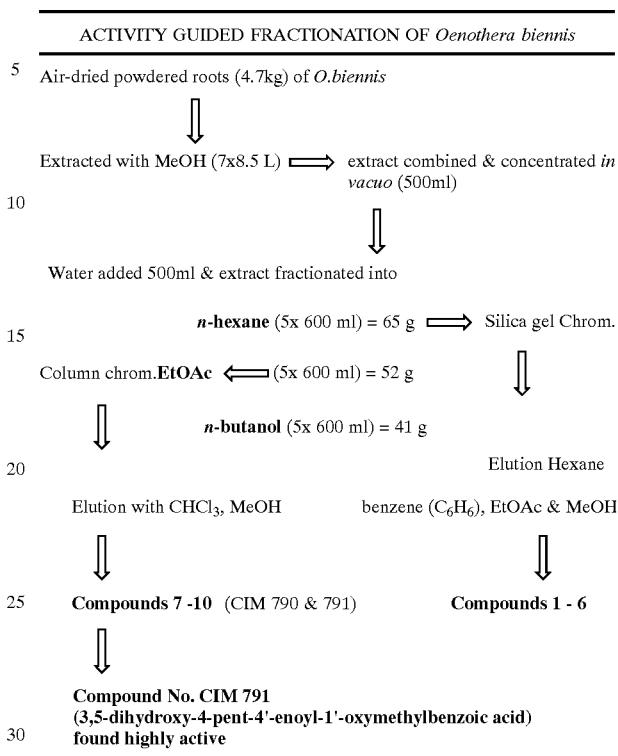

Each extract and fraction or sub fraction and or isolated pure compound is simultaneously tested for its antibacterial property using *S.epidermidis* culture in disc diffusion assay.

Silica gel chromatography of the ethyl acetate fractions of the methanol extractives of the root yielded compounds 7–10. CIM 791 has the following physical properties: IR spectrum, bands for COOH (1692 cm$^{-1}$), double bond (1612 cm$^{-1}$), COOCH$_3$ (1730 cm$^{-1}$) and phenol (PhOH) (3512 cm$^{-1}$); UV maxima at 215 and 278 nm; [M+] ion in the mass spectrum of 3 at m/z 266 is in agreement with the molecular formula $C_{13}H_{14}O_6$. The further identification properties and the NMR spectral data of this compound is described in *Indian J Chem.*, 38B, 1999, 705, incorporated herein. Table 2 depicts the 1-R-mass spectral structure of Oenostacin.

TABLE 2

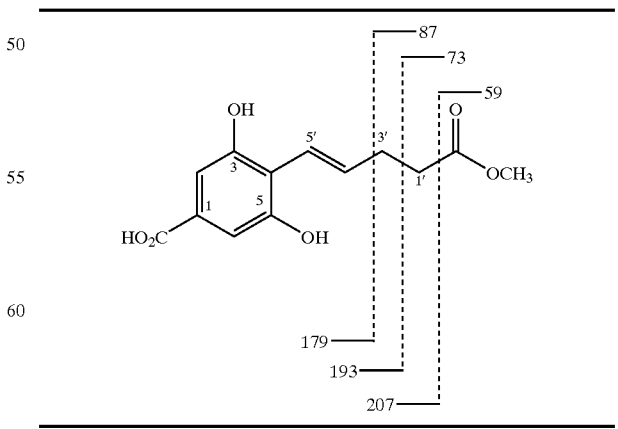

CIM 791 is tested for its minimal inhibitory concentration, which is a measure of the growth inhibitory potential of the compound and determined against *S. epidermidis* by two-fold broth dilution technique.

In the methods of the present invention, a pharmaceutical composition can be administered either orally, rectally, parenterally (intravenously, intramuscularly or subcutaneously), intracistemally, intravaginally, intraperitoneally, intravesically, locally (powders, ointments or drops), or as a buccal or nasal spray.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspension s may also contain one or more preserv atives, for example ethyl, or n ropyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Compositions for rectal administrations are preferably suppositories which can be prepared by mixing the compounds of the present invention with suitable nonirritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers or propellants as may be required. Ophthalmic formulations, eye ointments, powders, and solutions are also contemplated as being within the scope of this invention.

The compound of the present invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well-known to those skilled in the art.

The disclosures in this application of all articles and references, including patents, are incorporated herein by reference.

The invention is illustrated further by the following examples, which are not to be construed as limiting the invention in scope or spirit to the specific procedures described in them.

EXAMPLE 1

Extraction of Oenostacin

The air-dried and powdered roots (4.7 kg) of *O. biennis* are extracted with methanol (MeOH) (7×8.5 L) and the combined extract is concentrated in vacuo to 500 mL. Water is added and the extract then fractionated successively into n-hexane (5×600 mL, 65 g); EtOAc (5×600 mL, 52 g) and n-BuOH (5×600 mL, 41 g). The MeOH extract and the various solvent fractions form the initial material from which bioactivity guided fractionation is performed.

EXAMPLE 2

Each of the solvent fractions obtained from the powdered roots of *O. biennis* is tested for their antibacterial property. This is performed by single disc diffusion assay as per Bauer et al., 1966, (*American Journal of Clinical Pathology* 45: 493–496) with slight modifications. The discs are prepared (5 mm diameter made of Whatman #3 filter paper) by impregnating 8 µl of test compound and placing them on pre-inoculated agar surface. A disc containing only the solvent is used as the control. As evident from Table 3, the EtOAc fraction show significant antibacterial activity against *Staphylococcus epidermidis* and *Streptococcus mutans*. This indicates the presence of antibacterial substance in the EtOAc fraction of *O.biennis* roots. These results form the basis of further experimentation.

TABLE 3

Antibacterial activity of solvent extracts from roots of *O. biennis.*

| Extract @ 400 µg/disc | Diameter of the Zone of growth inhibition (mm) against | | |
|---|---|---|---|
| | S. epidermidis | S. mutans | P. aeruginosa |
| MeOH extract | — | — | — |
| Hexane extract | — | — | — |
| EtOAc extract | 08 | 08 | — |
| BuOH extract | — | — | — |

EXAMPLE 3

Tests of antibacterial activity

To isolate the antibacterial principle from the EtOAc fraction, a portion (19 g) of this fraction is chromatographed in a column over silica gel (800 g), eluting with varying proportions of chloroform ($CHCL_3$) and MeOH to afford four compounds. Each 100 mL fraction collected is monitored by TLC. One compound (CIM 791) is identified as 3,5-dihydroxy-4-pent-4'-enoyl-1'-oxymethylbenzoic acid (Oenostacin) based on NMR spectral data mentioned in *Indian J Chem.*, Vol 38B, 1999, 705. Table 4 indicates that the EtOAc fractions 3 and 4 possess the expected antibacterial activity against the test bacterial strains. The EtOAc fraction 4 exhibits growth inhibitory activity against *Pseudomonas aeruginosa* indicating the presence of a specific chemical compound in this fraction.

TABLE 4

Antibacterial activity of different fractions of EtOAc extract of roots of *O. biennis.*

| Extract @ 400 µg/disc | Diameter of the Zone of growth inhibition (mm) against | | |
|---|---|---|---|
| | S. epidermidis | S. mutans | P. aeruginosa |
| EtOAc. Fract-1 | — | — | — |
| EtOAc. Fract-3 | 08 | 09 | — |
| EtOAc. Fract-4 | 15 | 09 | 10 |

EXAMPLE 4

In order to identify the antibacterial chemical entities present in the EtOAc fraction 3 and 4 of *O.biennis* roots, the fractions are further run on silica gel column chromatography again eluting with varying proportions of chloroform and MeOH. Aliquots of eluate are run on TLC to check for the desired purity of the compound. The pure compounds thus obtained are analyzed for their antibacterial properties by two-fold broth dilution method to determine the minimal inhibitory concentration (MIC). The results indicate (Table 5) that one compound, CIM791, has strong antibacterial activity against *Staphylococcus epidermidis* since the MIC is found to be 31.5 µg/ml. Yet another compound, CIM-790, is found to possess low inhibitory activity against *Streptococcus mutans* MIC=625 µg/ml). The compounds CIM791 and 790 are identified as 3,5-dihydroxy-4-pent-4'-enoyl-1'-oxymethylbenzoic acid (Oenostacin) and gallic acid, respectively, using NMR spectral data.

TABLE 5

The minimal inhibitory concentration of Oenostacin against bacterial strains

| Compound | Minimal inhibitory concentration (MIC) | | |
|---|---|---|---|
| | S. epidermidis | S. mutans | P. aeruginosa |
| Gallic acid CIM-790 | — | 625 mg/ml | 1.25 mg/ml |
| Oenostacin CIM-791 | 31.5 g/ml | 1.25 mg/ml | — |

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method of treating a bacterial infection in a patient in need thereof, comprising administering to the patient a bacterial-treating composition comprising an effective amount of Oenostacin.

2. A method according to claim 1 in which the bacterial infection is caused by bacteria selected from streptococi and staphylococci.

3. A method according to claim 2 in which the bacterial infection is endocarditis.

4. A method according to claim 2 which the bacterial infection is caused caused by *S. epidermidis*.

5. A method as claimed in claim 1 wherein the concentration of Oenostacin in the composition is 1–200 µg/ml.

* * * * *